United States Patent [19]

Hall et al.

[11] Patent Number: 4,802,579

[45] Date of Patent: Feb. 7, 1989

[54] MEDICAL CONTAINER

[76] Inventors: S. Warren Hall; Jacquelyn L. O. Hall, both of 3 Cranleigh Court, Islington, Ontario, Canada

[21] Appl. No.: 26,875

[22] Filed: Mar. 17, 1987

[51] Int. Cl.[4] .......................................... B65D 83/10
[52] U.S. Cl. .................................. 206/366; 206/438; 206/364; 220/1 T
[58] Field of Search .............. 206/263, 364, 366, 438; 215/1 C, 6, 228; 81/3.25, 3.31, 3.08, 3.15; 30/329, 337, 339; 220/1 T

[56] References Cited

U.S. PATENT DOCUMENTS

| | | | |
|---|---|---|---|
| 2,588,687 | 3/1952 | Ajouelo | 81/3.08 |
| 3,940,002 | 2/1976 | Schiemann | 215/1 C |
| 4,287,794 | 9/1981 | Kubach et al. | 81/3.31 |
| 4,351,434 | 9/1982 | Elisha | 206/366 |
| 4,375,849 | 3/1983 | Hanifl | 206/366 |
| 4,452,358 | 6/1984 | Simpson | 206/366 |
| 4,466,538 | 8/1984 | Gianni | 206/370 |
| 4,466,539 | 8/1984 | Frauenhoffer | 206/320 |
| 4,494,652 | 1/1985 | Nelson et al. | 206/380 |
| 4,520,926 | 6/1988 | Nelson | 206/366 |
| 4,576,281 | 3/1986 | Kirksey | 206/366 |
| 4,580,688 | 4/1986 | Harris et al. | 206/366 |
| 4,600,112 | 7/1986 | Shillington et al. | 206/366 |

FOREIGN PATENT DOCUMENTS

| | | | |
|---|---|---|---|
| 2740335 | 3/1979 | Fed. Rep. of Germany | 206/63.5 |
| 1117155 | 2/1956 | France | 215/1 C |
| 496563 | 12/1955 | Italy | 81/3.08 |
| 2040268 | 8/1980 | United Kingdom | 206/360 |

Primary Examiner—David T. Fidei

[57] ABSTRACT

The medical container of the present application is designed to provide a simple method and structure for the disposal of medical needles, of the type for taking blood samples and similar applications. Needles of this type have a steel or metal shank portion through which the blood or liquid is drawn, a plastic collar intermediate the length of the steel shank for releasably engaging a barrel portion with a portion of the needle extending interior to the barrel. The needles are released from the barrel by screwing the plastic collar out of the barrel. The container assists in this operation and includes a needle release area, preferably a sunken recess, which has a needle receiving port having an enlarged area through which the needle and collar may pass and a restricted area for gripping the front portion of the plastic collar on the needle. The needle release area is shaped to provide the user with a mechanical advantage by using the barrel portion as a lever, forcing the collar into the restricted area of the needle release area in a manner to grip the collar and hold the same such that the barrel may be rotated to cause release of the needle. After the screw thread of the collar has been released from the barrel, the needle is then passed through the enlarged area, whereupon the needle falls through the enlarged area into the closed confines of the container.

7 Claims, 3 Drawing Sheets

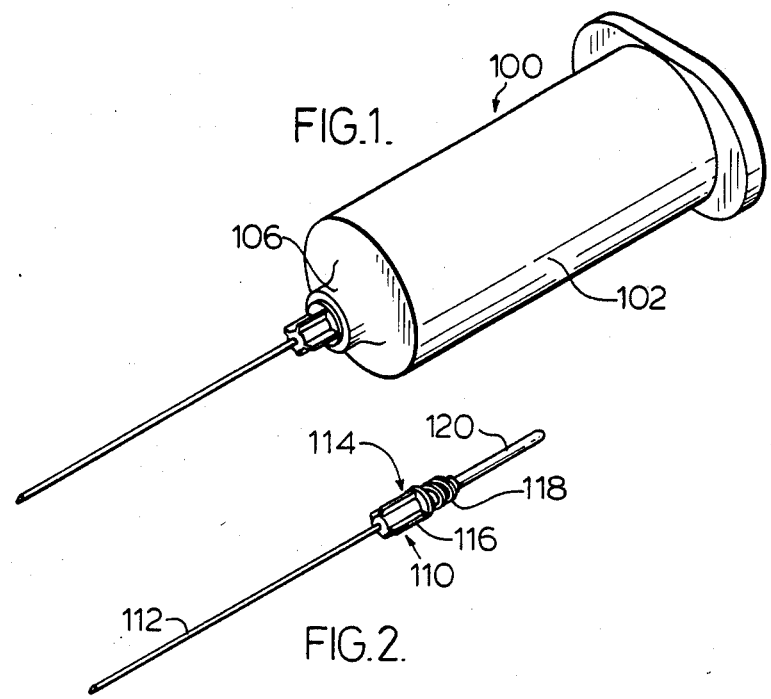
FIG. 1.
FIG. 2.
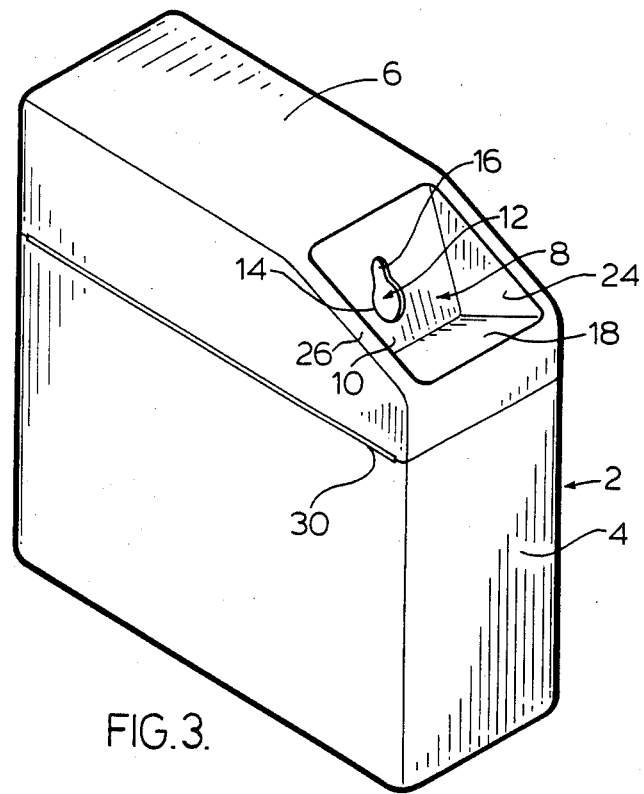
FIG. 3.

MEDICAL CONTAINER

BACKGROUND OF THE INVENTION

The present invention relates to a simplified container which is essentially closed and adapted to facilitate the release of a disposable needle from a reusable barrel. The disposable needles and reusable barrels of this type are generally used for taking blood samples, although the present invention is not so restricted.

In the past, a number of containers have been proposed for the disposal of medical needles of the type having a hollow steel portion through which a liquid is drawn, a collar intermediate the length of the steel portion adapted for engagement with a reusable barrel with the front of the collar having a gripping area to facilitate assembly of the needle in the barrel and release of the needle from the barrel. The needles once used, are then disposed of, whereas the barrel portion is reused. The barrel is preferrably of a plastic material and are well known in the industry. Similarly, there a number of manufacturers of needles of this type, all of which have the same general restrictions, i.e. a hollow steel portion, a plastic collar intermediate the length adapted for receipt within a reusable barrel and having a gripping area forward of the portion received within the barrel, with the hollow steel portion extending either side of the collar. These needles are packaged in a sterilized state in a closed plastic container which has two sheath portions, a front sheath portion received over the forward extending portion of the hollow steel portion and a second sheath which cooperates to cover the other end of the hollow steel portion and the screw connection of the collar which will be received in a barrel. In some cases, people in the past have kept the sheath portions and used these to dispose of the needle, however, for a number of safety reasons this is not a recommended procedure, as the likelihood of pricking oneself with the needle is fairly high. To overcome this problem, a number of containers have been proposed, where the user does not endanger themselves in disposing of the needle. The main problem with the prior art containers is with respect to the ability to grip the forward portion of the collar and hold the same, whereafter release of the barrel from the needle can be accomplished by screw-type separation. Some complicated containers have used mechanical levers to grip this collar area, which provide a very strong gripping but result in a complicated structure which is expensive and somewhat awkward to use. A disposable container has been proposed and is presently being marketed which defines a narrowing port into which the collar is inserted, with the needle and barrel moving in a perpendicular manner into the restricted area of the port to grip the collar to allow screw removal. The action used in this container requires a fair degree of dexterity and problems can result in that the nipple region of the barrel can be engaged with the large opening causing damage thereto, when it is moved into the restricted area. Therefore, the structure works satisfactorily when used in its intended manner, however, the structure allows various other variations to that method to be used which are not effective and thus reduce its value.

SUMMARY OF THE INVENTION

According to the present application, a simplified structure and method of removing a disposable needle from a reusable barrel is proposed, which advantageously uses the barrel as a lever to provide a mechanical advantage to assure gripping of the collar of the disposable needle. According to a preferred embodiment of the invention, a sunken recess is provided which cooperates to ensure that only the forward portion of the collar is engaged in the gripping area of a needle receiving port provided in the sunken recess, such that damage to the nipple region of the barrel is avoided. The needle receiving port is provided in a restricted area of the sunken recess which is shaped such that the nipple of the barrel cannot come into damaging contact with the enlarged area of the needle receiving port, as it is positioned in a lower region of the recess with the barrel contacting faces of the recess which limit insertion of the nipple into the port. To remove a needle, the barrel and needle must be appropriately angled to insert the collar within the enlarged area of the needle receiving port, and thereafter the barrel and needle moved through an angle which forces the collar into the restrictd area of the needle receiving port. The collar of the needle held in the engaging portion of the needle receiving port, restricts rotational movement of the collar and a pivot point is provided which strikes the barrel portion intermediate its length to provide the mechanical advantage to increase the gripping force on the collar. Thus, the barrel is used as a lever to increase the gripping force and rotation of the barrel will allow removal of the needle as it is held in the needle receiving port. Once the needle has been released from the barrel, it can then move to the enlarged area where it can fall through the port and into the closed confines of the container.

BRIEF DESCRIPTION OF THE DRAWINGS

Preferred embodiments of the present invention are shown in the drawings wherein;

FIG. 1 is a perspective view of an assembled barrel and disposable needle;

FIG. 2 is a perspective view of the disposable needle;

FIG. 3 is a perspective view of the medical container;

DETAILED DESCRIPTION OF THE PREFERRED EMBODIMENTS

Figure 4:
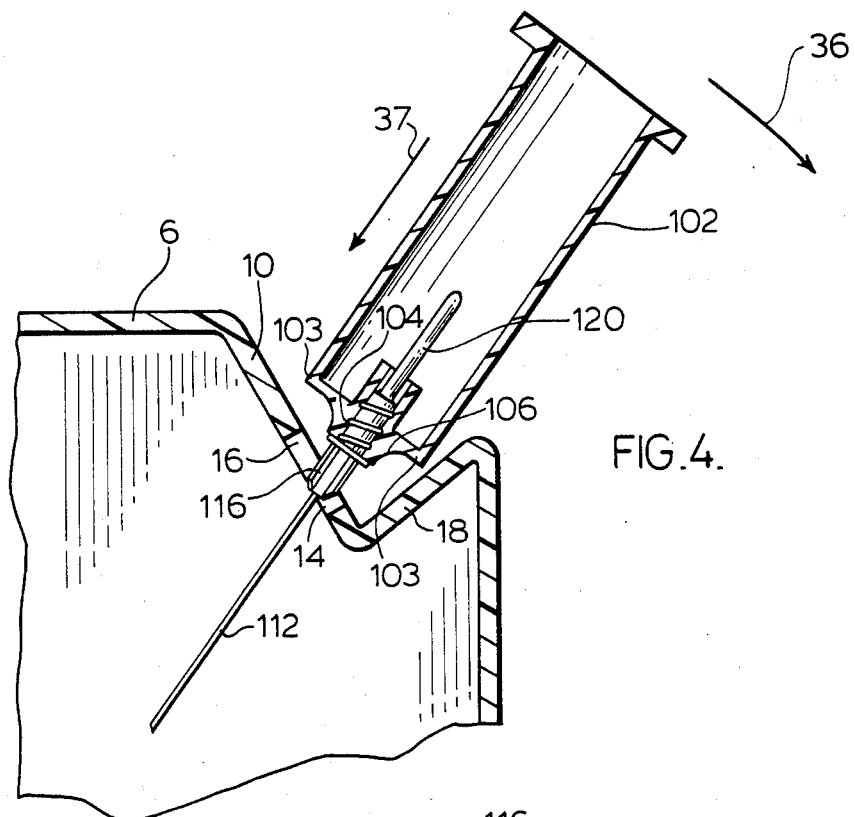
FIG. 4 is a sectional view of the needle receiving port showing insertion of the needle and barrel in preparation for engagement of the needle.

The assembled needle and barrel generally shown as 100 in the figures, includes a reusable barrel 102 having a threaded port 104 in the nipple region 106. The opposite end of the barrel is open for receiving vacuum tubes and the like, which when inserted over the rear portion of the hollow steel portion 112 of the needle, will draw blood or other fluids into the vacuum tube. Thus, in effect the barrel just provides a structure for receiving a vacuum tube or the like which cooperates with the disposable needle for collecting of liquid samples. The needle 110 includes a hollow steel portion 112 which extends either side of the collar 114.

The collar is of a plastic material and includes a front gripping area 116, in this case having a cylindrical interior section, with a number of outwardly extending fins for gripping of the collar. The collar also includes a threaded portion 118 for receipt in the threaded port 104 of the barrel 102. In some cases, the rear portion of the hollow steel portion 112 will include a multi use shield shown as 120 collapses along the length of the hollow steel portion 112 when a vacuum tube is inserted in a barrel and removal of the vacuum tube allows the multi use shield to again return and cover the back portion of the needle. This avoids dripping of blood etc. from the back portion of the needle which may contaminate the reusable barrel 102.

The container 2 includes a base portion 4 and a top portion 6 which cooperate to define a closed container. In this case, the top portion includes a needle release area 8 which preferably is a sunken recess as shown in FIG. 3. The recess includes a needle receiving port 12 having an enlarged area 14 for allowing a needle and collar to pass therethrough. The port also includes a restricted area for gripping of the front area 116 of a collar when a needle is received in the needle receiving port. This restricted area 16 opens onto the enlarged area 14. The sunken recess 8 includes a back face 10 which has the needle receiving port 12 and associated with the back face is an extending face 18, which is positioned to cooperate with a barrel 102 when a needle is to be released from the barrel. Preferably, the sunken recess includes side shields 24 and 26 to assure that the tip of the needle remains within the recess as the user seeks to pass the hollow portion 112 through the needle receiving port 12.

Figure 5:
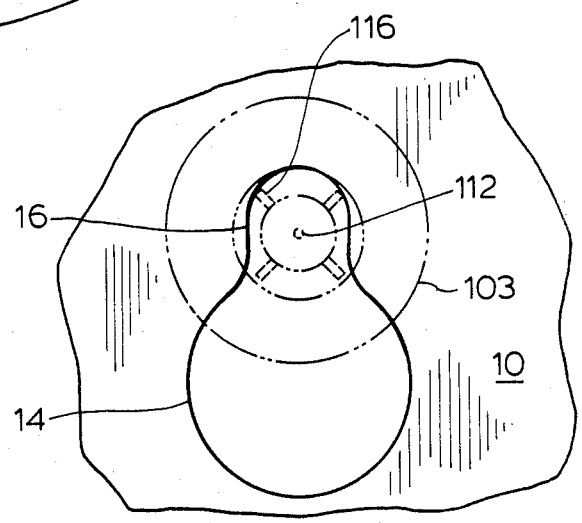
FIG. 5 is a back view of the needle receiving port showing the collar of the needle engaged in the restricted area of the port with the barrel beyond the engaging faces of the port.
Figure 6:
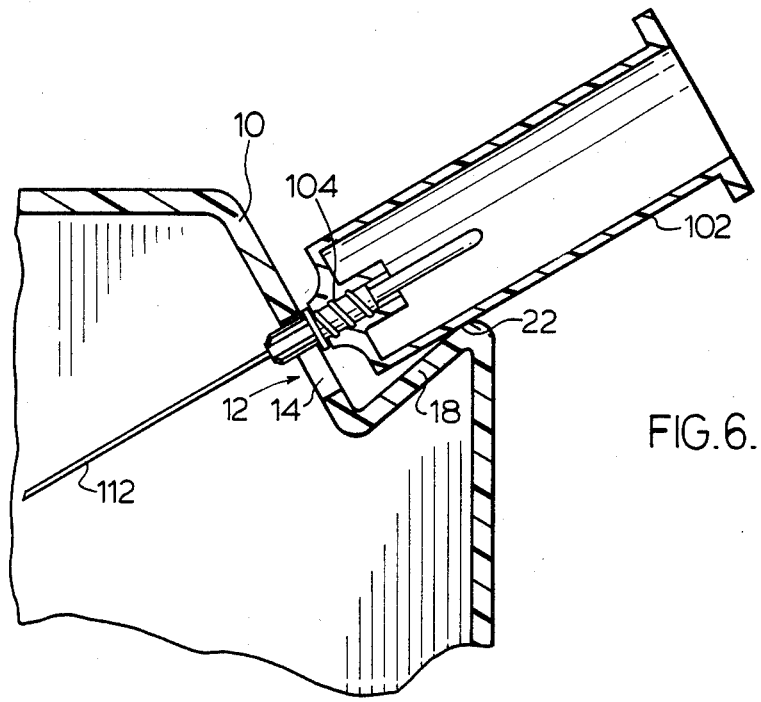
FIG. 6 is a sectional view of the needle receiving port with the needle engaged in a restricted area of the port.
Figure 7:
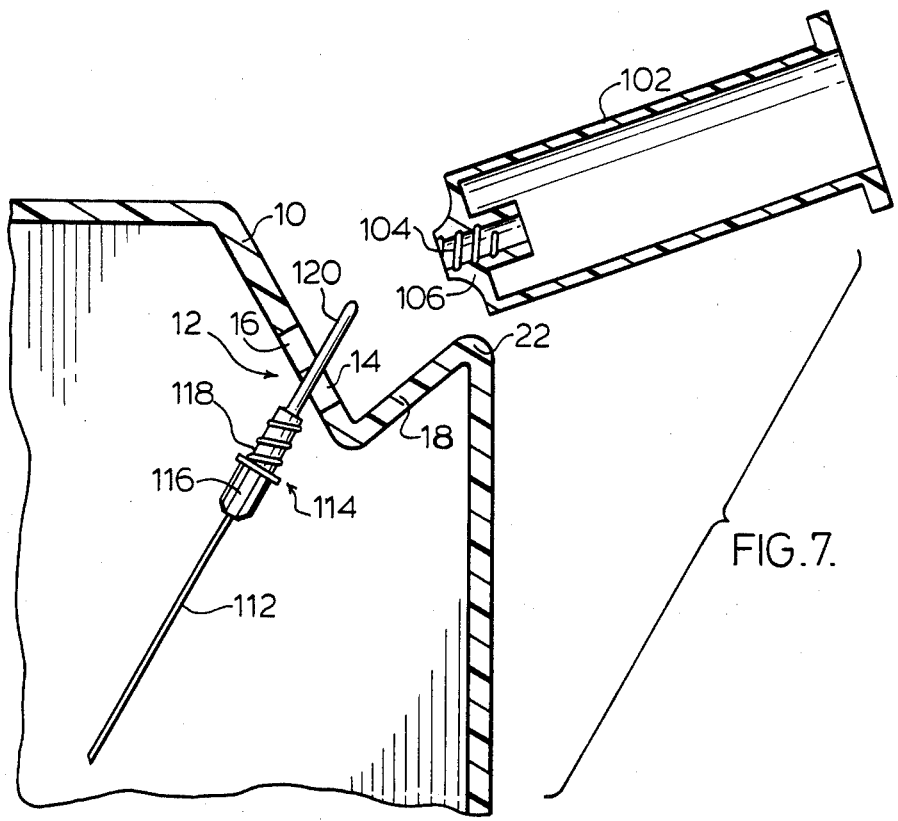
FIG. 7 is a view showing the reusable barrel released from the needle with the needle falling into the medical container.

The cooperation between the container and the assembled barrel and needle can be appreciated from FIGS. 4 through 7. As can be seen, the assembled needle and barrel are orientated to allow the front portion of the hollow steel portion 112 of the needle to pass through the needle receiving port 12. The front portion 116 of the collar 114 is inserted in the enlarged area 14 of the needle receiving port 12, whereafter the barrel is forced into engagement with the pivot point defined by the lip region 22, and further movement of the barrel of the container in direction of arrow 36 in a manner to urge the front gripping area 116 of the collar 114 into the restricted area 16 of the needle receiving port 12. A needle which has been so positioned as generally shown in FIGS. 5 and 6.

It should be noted that the nipple region 106 of the barrel 102 cannot easily gain access, if at all, to the enlarged area of the needle receiving port 12 as the periphery of the barrel, generally shown as 103 comes in contact with the back face 10 and the extending face 18, thus limiting the depth with which the barrel can extend into the recess. Therefore, in effect, this enlarged area 14 of the needle receiving port 12 has been positioned at a deep area in the sunken recess which is not accessible to, or is essentially non accessible by the nipple region 106 of the barrel 102. The upper area which is restricted and generally shown as 16 of the needle receiving port 12. is sized to be smaller than the nipple region 106 and, therefore, the nipple region 106 cannot gain access to that portion of the needle receiving port. Movement of the barrel in the direction of arrow 36 forces the front gripping area of the collar into the restricted area 16 of the needle receiving point. The movement of the barrel is limited as the barrel 102 strikes the lip region generally shown as 22 in FIG. 6. This lip region 22 is spaced from the needle receiving port 12 and acts as a pivot point such that pressure urging the barrel in the direction of arrow 36 results in a strong gripping force of the collar 116 held in the restricted area 16 which allows the screw removal of the barrel from the held collar 114. If any slippage of the collar within the port 116 should result, for example, if damage has occurred to the collar, additional pressure may be applied to the barrel to increase the gripping force. Once the barrel has been released from the collar 114, the needle may then move to the enlarged area of the needle receiving port, to allow the collar to pass through the enlarged area 14 and into the closed confines of the container 2.

The medical container generally shown as 2 is preferrably made of a plastic material of a suitable strength and hardness, such that needles of this type cannot pierce therethrough in the normal use of the container. For example, the walls of the container should not be of softness or thin section, which would allow the passage of the needles through the walls of the container simply by their movement within the container. Similarly, these materials can be selected and thicknesses selected which may still allow a needle to pass therethrough if a person tries to force the needle through, but should be of a thickness such that this does not occur in the normal operation and use of the container. It is preferred that the present invention be used as a disposable container which may collect anywhere from several used needles to hundreds of used needles. It can be appreciated that the exact sizing of the container is not critical, however, it is generally felt that the container should hold anywhere from 50 to 250 needles.

The container generally shown in FIG. 3 has been horizontally split to define the top portion 6 and the base portion 4. A integral molded hinge has been provided as generally shown as 30. The container of this type can be made as one piece, and would have a snap locking fit (not shown) between the top portion 6 and the base 4 to maintain the closed container generally shown in FIG. 3. In some circumstances, it may be desirable to have the top portion releasable from the base portion 4, by use of the integral hinge 30, however, it is anticipated that a locking relationship between the top portion 6 and the base portion 4 should be provided to ensure that the disposed needles are maintained within the closed confines of the container. Once the container is filled or the user decides that it is time to dispose of the container, it may be desirable to close the needle receiving port 12. This could be closed with a plug member, (not shown) or by applying a tape over the back face 10 or the sunken recess of the container. It is also possible to integrally mold a hinged flap to effect closure of the sunken container, although, in the most simple application, it is not believed that this will be necessary.

It is preferred that the sunken recess including the back face 10, the extending face 18 with the lip 22 and the needle receiving port 12, cooperate such that the longitudinal axis of the assembled needle and barrel when received by the container to remove a needle, with the front gripping area 116 in the restricted area 16 of the needle receiving port 12, is generally perpendicular to the back face 10. The point to recognize, is that, movement of the barrel in direction of arrow 36 should be limited by the restricted area 16, whereby the liklihood of the front gripping area 116 slipping out of the port is reduced. Once the collar has moved past the general perpendicular orientation, the effective area of gripping of front gripping area 116 continues to reduce and the gripping force is also reduced. Put another way, it is desirable that the force exerted on the container by the gripping area 116 is along the surface of the back face 10, as opposed to at an angle thereto, which urges release of the collar. As you depart from this relationship by moving the barrel through a greater angle, the effective gripping force will reduce and the likelihood of the gripping area 116 leaving the restricted area 16 increases.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. In a container, a disposable medical needle engaging region comprising a notched area having a camming surface and an associated recess in an adjacent angled surface, said recess having a widened region for allowing entry of a disposable medical needle and a gripping region associated with said widened region sized to engage a plastic connecting piece of such needle when forced into engagement therewith, said gripping region being appropriately spaced from said camming surface to cooperate with a support of such needle to effect gripping of such plastic region in said gripping region by using such support as a lever against said camming surface urging such plastic region into said gripping region.

2. A method of removing a disposable medical needle from a reusable barrel, such disposable needle being of the type having a plastic collar intermediate the length of the needle for providing a screw-type connection with such barrel comprising;

inserting the needle through a recess having a wide area and a reduced gripping region such that the plastic collar is inserted into said recess at the wide area, forcing said collar into said reduced gripping region by moving the barrel against a camming surface spaced from the gripping region and using the barrel and cam as a lever to effect the necessary grip of said collar in said reduced gripping region, turning the barrel as the collar is held in said gripping region to release the needle from the barrel, allowing said collar to return to the wide area and pass through the recess into a container.

3. A container for receiving disposable medical needles having a collar portion for affecting securement with a reusable barrel, said container comprising;

an upper region having a needle removing area including a camming surface spaced from a needle receiving recess, said recess having a wide area oversized relative to such collar and a restricted area for engaging the collar, and holding the same against rotation, said camming surface being positioned to engage the side of such barrel intermediate the length thereof when a needle is inserted into the recess with the collar in the recess, said restricted area being positioned to engage such collar as the barrel is used as a lever in cooperation with said camming surface to effect sufficient gripping of said collar to remove such barrel by rotation thereof as said collar is held, whereafter said collar can return to said wide area and allow such needle to pass into the container.

4. A container as claimed in claim 3 wherein said recess opens upwardly and provides a funnel like region for accepting liquids into said container.

5. A container as claimed in claim 3 wherein said recess includes side portions such that a needle can only be withdrawn from said recess in one general direction.

6. A container as claimed in claim 3 formed from an injection moldable plastic.

7. A container as claimed in claim 3 wherein said container is at least essentially of a one piece construction.

* * * * *